(12) United States Patent
Goshayeshgar et al.

(10) Patent No.: US 11,413,080 B2
(45) Date of Patent: Aug. 16, 2022

(54) CURVED INFLATABLE BONE TAMP WITH VARIABLE WALL THICKNESS

(71) Applicant: MEDTRONIC HOLDING COMPANY SÀRL, Tolochenaz (CH)

(72) Inventors: Mojan Goshayeshgar, Atherton, CA (US); Samuel V. Bolosan, San Jose, CA (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 183 days.

(21) Appl. No.: 16/984,388

(22) Filed: Aug. 4, 2020

(65) Prior Publication Data

US 2020/0360069 A1 Nov. 19, 2020

Related U.S. Application Data

(62) Division of application No. 15/784,254, filed on Oct. 16, 2017, now Pat. No. 10,779,870.

(51) Int. Cl.
| | |
|---|---|
| *A61B 17/88* | (2006.01) |
| *A61M 25/00* | (2006.01) |
| *A61B 17/00* | (2006.01) |
| *A61M 25/10* | (2013.01) |

(52) U.S. Cl.
CPC ...... *A61B 17/8855* (2013.01); *A61B 17/8802* (2013.01); *A61B 2017/00867* (2013.01); *A61M 25/0041* (2013.01); *A61M 25/1002* (2013.01); *A61M 2025/0039* (2013.01); *A61M 2025/1004* (2013.01); *A61M 2025/1031* (2013.01)

(58) Field of Classification Search
CPC .............. A61B 17/885; A61B 17/8852; A61B 17/8855; A61B 17/8858; A61B 17/7097
See application file for complete search history.

(56) References Cited

U.S. PATENT DOCUMENTS

| | | | |
|---|---|---|---|
| 5,320,605 A | 6/1994 | Sahota | |
| 5,334,146 A | 8/1994 | Ozasa | |
| 5,961,536 A | 10/1999 | Mickley et al. | |
| 6,488,653 B1 | 12/2002 | Lambardo | |
| 6,544,224 B1 | 4/2003 | Steese-Bradley | |
| 6,554,795 B2 | 4/2003 | Bagaoisan et al. | |
| 6,607,545 B2 | 8/2003 | Kammerer et al. | |
| 6,951,569 B2 | 10/2005 | Nohilly et al. | |

(Continued)

OTHER PUBLICATIONS

European Search Report, European Patent Office, EP 18195882.8-1132, dated Mar. 21, 2019.

*Primary Examiner* — Anu Ramana
(74) *Attorney, Agent, or Firm* — Sorell, Lenna & Schmidt, LLP

(57) ABSTRACT

A curved inflatable bone tamp includes an outer shaft defining a passageway. An inner shaft is positioned within the passageway. The inner shaft extends between opposite first and second end. The inner shaft defines a lumen. The inner shaft is curved between the first end and the second end. A first leg of a balloon is coupled to the outer shaft and a second leg of the balloon is coupled to the inner shaft such that a material can flow through the lumen and into the balloon to inflate the balloon. The balloon includes a wall having a variable thickness between the legs when the balloon is uninflated and a uniform thickness between the legs when the balloon is inflated. Kits, systems and methods are disclosed.

20 Claims, 10 Drawing Sheets

(56) References Cited

U.S. PATENT DOCUMENTS

| | | |
|---|---|---|
| 7,175,607 B2 | 2/2007 | Lim et al. |
| 7,736,292 B2 | 6/2010 | Hermann |
| 8,221,349 B2 | 7/2012 | Auyoung et al. |
| 8,262,609 B2 | 9/2012 | Sapida et al. |
| 8,740,842 B2 | 6/2014 | Weber et al. |
| 9,204,915 B2 | 12/2015 | Arthur et al. |
| 9,295,510 B2 | 3/2016 | Auyoung |
| 9,717,551 B2* | 8/2017 | Krueger .............. A61B 18/1477 |
| 2003/0191452 A1* | 10/2003 | Meglin ................ A61M 27/00 |
| | | 604/537 |
| 2004/0092946 A1* | 5/2004 | Bagga ................ A61B 17/1617 |
| | | 606/93 |
| 2007/0010845 A1 | 1/2007 | Gong et al. |
| 2007/0066987 A1* | 3/2007 | Scanlan ............. A61B 17/3472 |
| | | 600/564 |
| 2009/0131867 A1* | 5/2009 | Liu .................... A61M 25/0136 |
| | | 604/272 |
| 2009/0143634 A1 | 6/2009 | Benson et al. |
| 2009/0326538 A1 | 12/2009 | Sennett et al. |
| 2010/0298832 A1* | 11/2010 | Lau .................... A61B 17/8855 |
| | | 606/86 R |
| 2011/0196499 A1* | 8/2011 | Boucher ............... A61F 2/4601 |
| | | 623/17.16 |
| 2011/0264099 A1* | 10/2011 | Quinto ............... A61B 17/8819 |
| | | 606/94 |
| 2012/0004594 A1* | 1/2012 | Schulz ................ A61M 1/0058 |
| | | 604/500 |
| 2012/0197319 A1* | 8/2012 | Auyoung ........... A61B 17/7097 |
| | | 606/86 R |
| 2013/0165942 A1* | 6/2013 | Tan-Malecki ...... A61B 17/8855 |
| | | 606/86 R |
| 2013/0197563 A1* | 8/2013 | Saab .................. A61B 17/8855 |
| | | 606/191 |
| 2013/0345709 A1* | 12/2013 | Burger ............... A61B 17/8811 |
| | | 606/94 |
| 2013/0345765 A1* | 12/2013 | Brockman ......... A61B 17/1642 |
| | | 606/86 R |
| 2014/0005711 A1* | 1/2014 | Saab ................. B01L 3/502746 |
| | | 606/191 |
| 2016/0051306 A1* | 2/2016 | Sasaki ............... A61B 17/1659 |
| | | 606/86 R |
| 2016/0136397 A1 | 5/2016 | Konstantino et al. |
| 2016/0250455 A1 | 9/2016 | Ahn |

\* cited by examiner

CURVED INFLATABLE BONE TAMP WITH VARIABLE WALL THICKNESS

CROSS-REFERENCE TO RELATED APPLICATION

This application is a divisional of U.S. patent application Ser. No. 15/784,254, filed Oct. 16, 2017, which is expressly incorporated herein by reference, in its entirety.

TECHNICAL FIELD

The present disclosure generally relates to medical devices for the treatment of bone disorders, and more particularly to devices and methods for treating spinal disorders, such as, for example, vertebral compression fractures.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting one or more balloons, such as, for example, compliant balloons inside a fractured vertebral body. The balloon or balloons are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

However, conventional spinal fracture treatment procedures lack a balloon that can be inflated to have a curved configuration when the balloon has a maximum volume and pressure necessary for a kyphoplasty procedure. Conventional balloons typically have very thick walls and are made of a compliant material. The wall thins out when the balloon is inflated. Since inflation of the balloon is symmetric, the wall will thin out uniformly, and the outer arch of the balloon, which is longer than an inner arch of the balloon, will be thinner than the inner arch when the balloon is inflated. Indeed, once inflation starts, the outer arch will start thinning out further than the inner arch, which will create a path of least resistance outward on the outer arch of the balloon. This will create an off-axis skewed kidney shape inflation. Such variation of the wall thickness of the balloon when the balloon is inflated makes the balloon ineffective for balloon kyphoplasty procedures that require a curved balloon. This disclosure describes improvements over these prior art technologies.

SUMMARY

New devices and methods are provided for the treatment of bone disorders, and more particularly devices and methods for treating spinal disorders, such as, for example, vertebral compression fractures. In some embodiments, a curved inflatable bone tamp includes an outer shaft defining a passageway. An inner shaft is positioned within the passageway. The inner shaft extends between opposite first and second end. The inner shaft defines a lumen. The inner shaft is curved between the first end and the second end. A first leg of a balloon is coupled to the outer shaft and a second leg of the balloon is coupled to the inner shaft such that a material can flow through the lumen and into the balloon to inflate the balloon. The balloon includes a wall having a variable thickness between the legs when the balloon is uninflated and a uniform thickness between the legs when the balloon is inflated.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
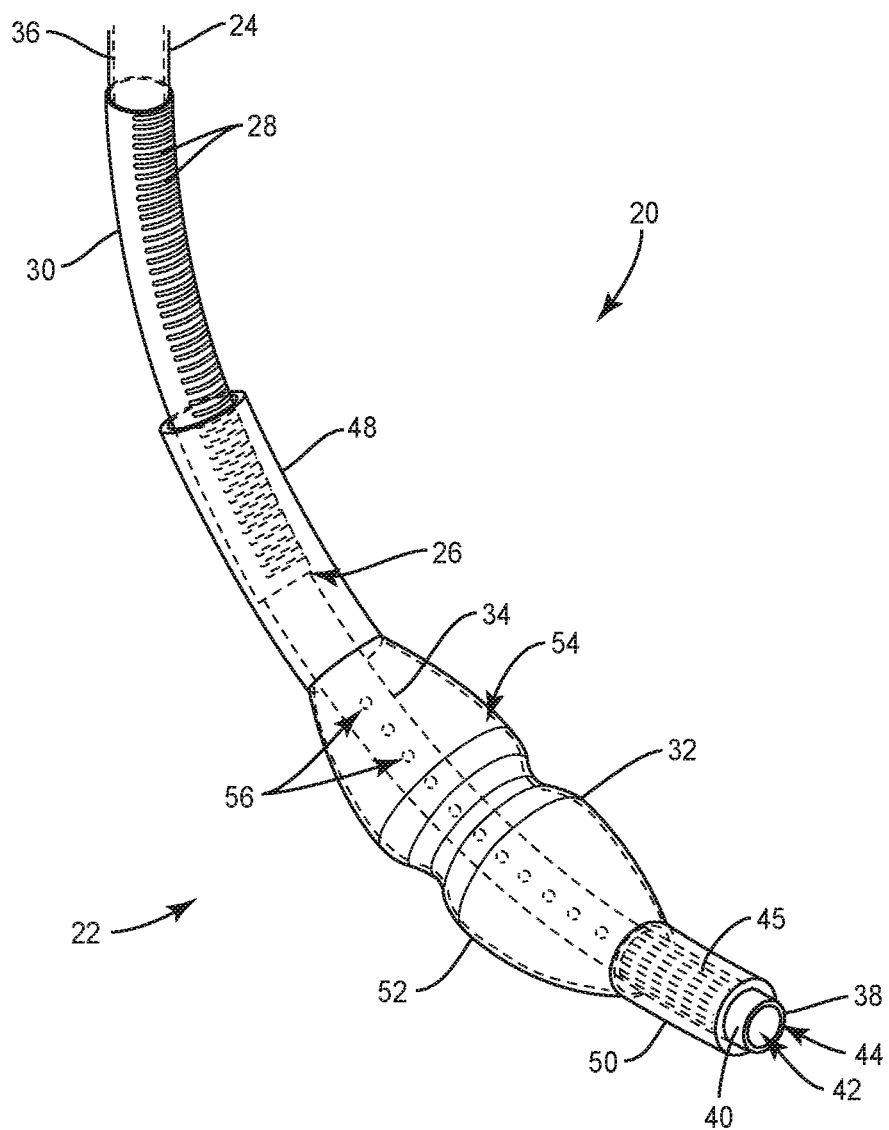
FIG. 1 is a perspective view, in part phantom, of a surgical instrument in accordance with the principles of the present disclosure.

In some embodiments, the present disclosure relates to a system that includes a curved high pressure balloon catheter for unipedicular kyphoplasty. The system comprises a nested cannula and curved stylet to access a vertebral body through a unipedicular access. The curved stylet will create a pilot hole for positioning the curved balloon catheter through a midline of the vertebral body. The balloon catheter includes a curved super-elastic metallic inner tube, such as, for example, an inner tube made of Nitinol. The balloon catheter further includes a straight metallic outer shaft, a proximal design to connect to an inflation syringe and a distal high pressure balloon with a variable wall thickness when the balloon is uninflated or only partially inflated.

In some embodiments, the high pressure balloon is formed with variable wall thickness when the balloon is uninflated or only partially inflated to improve the performance of inflation when it is inflated. The balloon will have a uniform thickness when inflated to improve balloon performance during a balloon kyphoplasty procedure. The variable wall when the balloon is uninflated or only partially inflated will improve the deflated profile and enhance the removal process. In some embodiments, the high pressure balloon is formed to be thicker on an outer cue or arch of the balloon and thinner on an inner curve or arch of the balloon. When the balloon is inflated, it will plastically deform to a more consistent wall thickness. The ratio of maximum to minimum wall thickness can be optimized for each size based on inflation volume and pressure. This improved design allows for a higher maximum inflation volume and better removal through an access cannula of the system. Providing a curved balloon that has a variable wall thickness when uninflated or only partially inflated and a uniform thickness when inflated will provide a controlled and uniform inflation shape.

It is envisioned that the disclosed curved balloon catheter can be used for unipedicular kyphoplasty in patients with one or more vertebral compression fractures or as an adjunctive to local tumor control interventions. In some embodiments, the balloon is specifically targeted for a vertebral body and balloon kyphoplasty so that a shape of the balloon follows an anterior wall of the vertebral body. This will dictate a certain radius of curvature (i.e. about 25 mm) for the balloon to be positioned more anterior and passed the midline and to inflate to an optimum shape to cover the anterior ⅔ of the vertebral body for treatment of vertebral compression fractures.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" comprises any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be comprised within the invention as defined by the appended claims.

This disclosure is directed to an inflatable bone tamp, such as, for example, a balloon catheter system 20. In some embodiments, the components of balloon catheter system 20 can be fabricated from biologically acceptable materials suitable for medical applications, including metals, synthetic polymers, ceramics and bone material and/or their composites, depending on the particular application and/or preference of a medical practitioner. For example, the components of balloon catheter system 20, individually or collectively, can be fabricated from materials such as stainless steel alloys, commercially pure titanium, titanium alloys, Grade 5 titanium, super-elastic titanium alloys, cobat-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of balloon catheter system 20 may have material composites, including the above materials, to achieve various desired characteristics such as strength, rigidity, elasticity, compliance, biomechanical performance, durability and radiolucency or imaging preference. The components of balloon catheter system 20, individually or collectively, may also be fabricated from a heterogeneous material such as a combination of two or more of the above-described materials. The components of balloon catheter system 20 may be monolithically formed, integrally connected or comprise fastening elements and/or instruments, as described herein.

Balloon catheter system 20 includes a curved inflatable bone tamp 22 comprising an outer shaft, such as, for example a shaft 24 defining a passageway 26. In some embodiments, passageway 26 has a uniform diameter along an entire length of shaft 24. In some embodiments, passageway 26 may have various cross section configurations, such as, for example, circular, oval, oblong, triangular, rectangular, square, polygonal, irregular, uniform, non-uniform, variable, tubular and/or tapered. In some embodiments, shaft 24 may at least initially have a straight configuration, and may be bent to have a curved configuration, as discussed herein. In some embodiments, shaft 24 may be pre-bent to have a curved configuration. In some embodiments, shaft 24 may include one or a plurality of surface features, such as, for example, ridges 28 to facilitate bending of shaft 24 in a controlled manner. Adjacent ridges 28 define a channel therebetween. As shown in FIG. 1, ridges 28 are disposed along shaft 24 in a linear, serial configuration such that ridges 28 extend parallel to one another to allow shaft 24 to bend about ridges 28. In some embodiments, ridges 28 extend only along a portion of a length of shaft 24. In some embodiments, ridges 28 extend only an entire length of shaft 24. As shown in FIG. 1, ridges 28 each extend perpendicular to a length of shaft 24. However, it is envisioned that ridges 28 may be disposed at alternate orientations, relative to the length of shaft 24, such as, for example, transverse and/or other angular orientations such as acute or obtuse, co-axial and/or may be offset or staggered, depending upon, for example, the desired curvature of shaft 24.

In some embodiments, shaft 24 comprises a metallic material. In some embodiments, shaft 24 is laser cut, braided, or coiled. In some embodiments, shaft 24 is coated with a material, such as, for example, a polymer 30 configured to facilitate bonding of an inflatable member, such as, for example, a balloon 32 to shaft 24, as discussed herein. In some embodiments, polymer 30 can also encapsulate and seal the laser cut, braid, or coil to prevent material ingress or egress through a thickness of shaft 24 that is coated with polymer 30. In some embodiments, ridges 28 are formed by the metallic material. In some embodiments, ridges 28 are formed by polymer 30. In some embodiments, ridges 28 are formed by the metallic material and polymer 30. In some embodiments, only a distal portion of shaft 24 is coated with polymer 30. In some embodiments, only a portion of shaft 24 that is bonded to balloon 32 is coated with polymer 30. In some embodiments, only portions of shaft 24 that are bonded to balloon 32 and include ridges 28 are coated with polymer 30. In some embodiments, shaft 24 is coated with polymer 30 along an entire length of shaft 24. In some embodiments, shaft 24 is covered with polymer 30 along at least a portion of shaft 24. In some embodiments, polymer 30 includes a thermoplastic polymer, such as, for example, thermoplastic polyurethane (TPU). In some embodiments, polymer 30 includes a elastomeric polymer, such as, for example, a thermoplastic elastomer (TPE).

An inner shaft, such as, for example, a shaft 34 is positioned within passageway 26. Shaft 34 extends between an end 36 an opposite end 38. End 36 is positioned within passageway 26 and end 38 is positioned outside of passageway 26. Shaft 34 is curved between end 36 and end 38. In some embodiments, shaft 34 is pre-bent to be curved between end 36 and end 38 such that when shaft 34 is inserted through passageway 26, shaft 34 causes shaft 24 to move from a straight configuration to a curved configuration. In some embodiments, shaft 34 is pre-bent to have a uniform radius of curvature. In some embodiments, shaft 34 is pre-bent to have a radius of curvature that varies along a length of shaft 34. In some embodiments, shaft 34 comprises a shape memory alloy, such as, for example, a super-elastic shape memory alloy. In some embodiments, shaft 34 comprises Nitinol. In some embodiments, shaft 34 is laser cut, braided, or coiled. In some embodiments, shaft 34 is coated with a material, such as, for example, a polymer 40 configured to facilitate bonding of balloon 32 to shaft 34, as discussed herein. In some embodiments, polymer 40 can also encapsulate and seal the laser cut, braid, or coil of shaft 34 to prevent material ingress or egress through a thickness of shaft 34 that is coated with polymer 40. In some embodiments, shaft 34 includes a rigid material, such as, for example, stainless steel (SST) or nickel titanium (NiTi), wherein at least a portion of shaft 34 includes one or more laser cuts to provide shaft 34 with the pre-bent shape. In some embodiments, the laser cuts are uniaxial. In some embodiments, the laser cuts are multiaxial. In some embodiments, the portion of shaft 34 that includes the laser cuts is jacketed or covered with polymer 40. In some embodiments, polymer 40 includes a thermoplastic polymer, such as, for example, thermoplastic polyurethane (TPU). In some embodiments, polymer 40 includes an elastomeric polymer, such as, for example, a thermoplastic elastomer (TPE).

Figure 2:
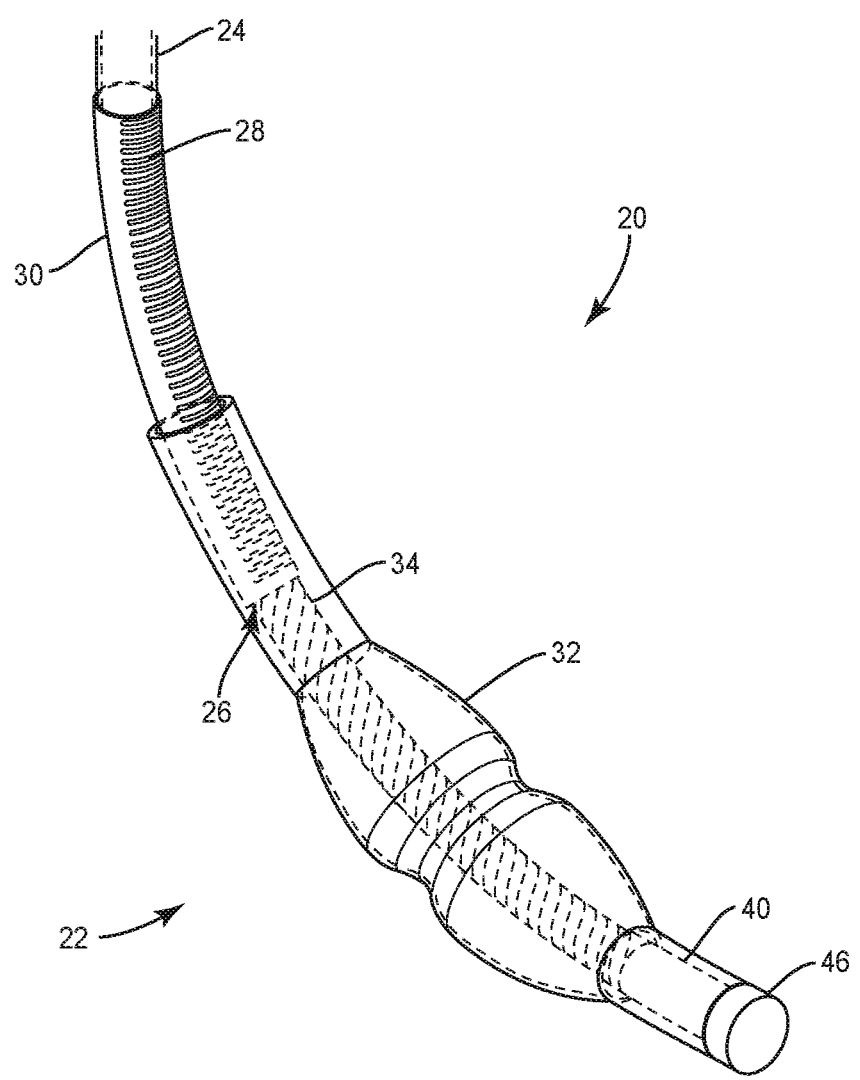
FIG. 2 is a perspective view of one embodiment of the surgical instrument shown in FIG. 1.

Shaft 34 defines a lumen 42 configured to move an inflation material, such as, for example, air, saline, or a contrast solution into and out of balloon 32 to move balloon 32 between an uninflated configuration and an inflated configuration, as discussed herein. In some embodiments, lumen 42 has a uniform diameter along an entire length of shaft 34. In some embodiments, lumen 42 may have various cross section configurations, such as, for example, circular, oval, oblong, triangular, rectangular, square, polygonal, irregular, uniform, non-uniform, variable, tubular and/or tapered. In some embodiments, a distal end of lumen 42 is closed to prevent the inflation material from moving out of lumen 42 through a distal end of lumen. In some embodiments, the distal end of lumen 42 includes an opening 44 to allow an instrument, such as, for example a guide wire to be inserted through lumen 42 such that the guide wire can extend through opening 44 and into tissue in order so that bone tamp 22 can be guided along the guide wire to a target location. In some embodiments, bone tamp 22 may include a removable cap 46, as shown in FIG. 2, for example. Cap 46 can be inserted onto shaft 34 such that cap 46 covers opening 44. In some embodiments, cap 46 can be variously connected with shaft 34, such as, for example, monolithic, integral connection, frictional engagement, threaded engagement, mutual grooves, screws, adhesive, nails, barbs and/or raised element. In some embodiments, polymer 40 includes a plurality of spaced apart grooves 45 that each extend parallel to a length of shaft 34, as shown in FIG. 1. Grooves 45 may be used to enhance fixation of cap 46 with shaft 34 and/or bonding of balloon 32 to shaft 34. In some embodiments, grooves 45 may be disposed at alternate orientations, relative to the length of shaft 34, such as, for example, transverse, perpendicular and/or other angular orientations such as acute or obtuse, co-axial and/or may be offset or staggered.

In some embodiments, balloon 32 is made from a resilient biocompatible material. In one embodiment, balloon 32 is a compliant balloon that resists stretching. In one embodiment, balloon 32 comprises polyolefin copolymer (POC), Polyurethane, Nylon. In one embodiment, balloon 32 is a non-compliant or semi-compliant balloon that stretches, at least to some degree. In one embodiment, balloon 32 comprises polyethylene terapthelate (PET). In some embodiments, balloon 32 can have various cross section configurations when balloon 32 is in the inflated configuration, such as, for example, oval, oblong, triangular, rectangular, square, polygonal, irregular, uniform, non-uniform, variable, tubular and/or tapered. In some embodiments, an outer surface of balloon 32 may have various surface configurations, such as, for example, smooth and/or surface configurations to enhance fixation with tissue, such as, for example, rough, arcuate, undulating, porous, semi-porous, dimpled, polished and/or textured.

Figure 4:
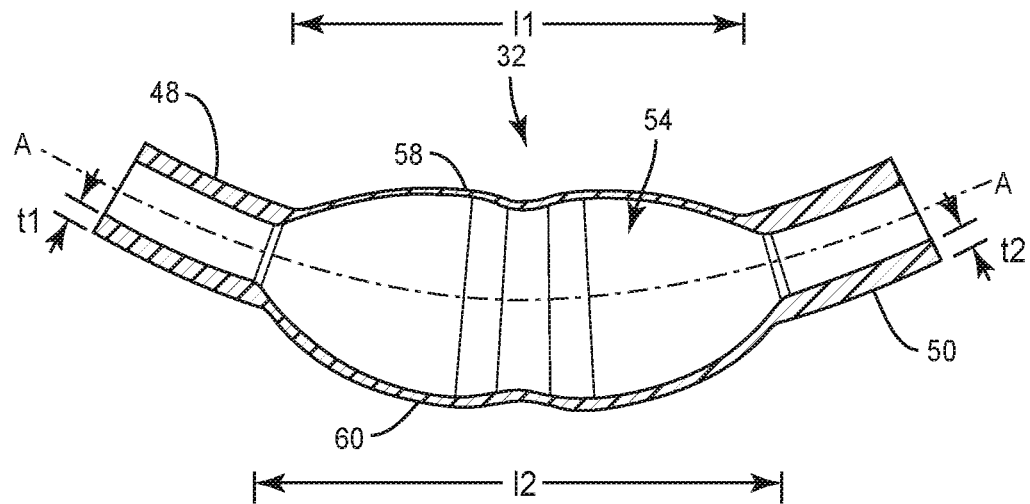
FIG. 4 is a side, cross sectional view of a component of the surgical instrument shown in FIG. 1.
Figure 5:
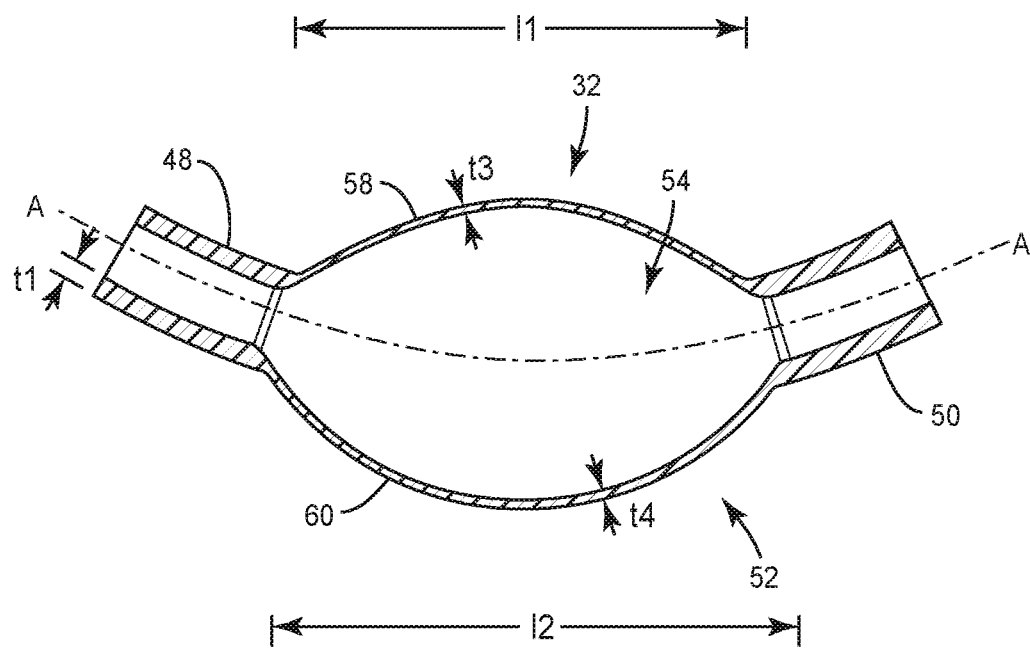
FIG. 5 is a side, cross sectional view of a component of the surgical instrument shown in FIG. 1.

Balloon 32 has a leg 48 that is bonded to polymer 30 to couple leg 48 to shaft 24. In some embodiments, leg 48 is bonded to polymer 30 using heat or an adhesive, for example. Bonding leg 48 to polymer 30 will provide a better bond than would bonding leg 48 to a portion of shaft 24 that does not include polymer 30 using heat or an adhesive. Balloon has a leg 50 that is bonded to polymer 40 to couple leg 50 to shaft 34. In some embodiments, leg 50 is bonded to polymer 40 using heat or an adhesive, for example. Bonding leg 50 to polymer 40 will provide a better bond than would bonding leg 50 to a portion of shaft 34 that does not include polymer 40 using heat or an adhesive. Balloon 32 has a body 52 that extends from leg 48 to leg 50. That is, body 52 is positioned between leg 48 and leg 50. Body 52 includes an inner surface that defines a chamber 54. Balloon 32 extends along a curved axis A, as shown in FIGS. 4 and 5, to provide balloon 32 with a curved configuration. In some embodiments, axis A has a continuous and/or constant radius of curvature. In some embodiments, axis A has a radius of curvature that is equal to the radius of curvature of shaft 32.

Figure 1A:
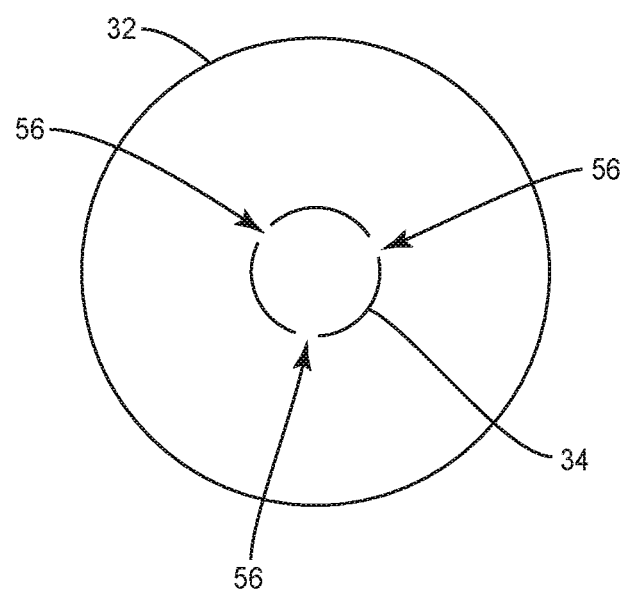
FIG. 1A is a cross sectional view of one embodiment of the surgical instrument shown in FIG. 1.
Figure 3:
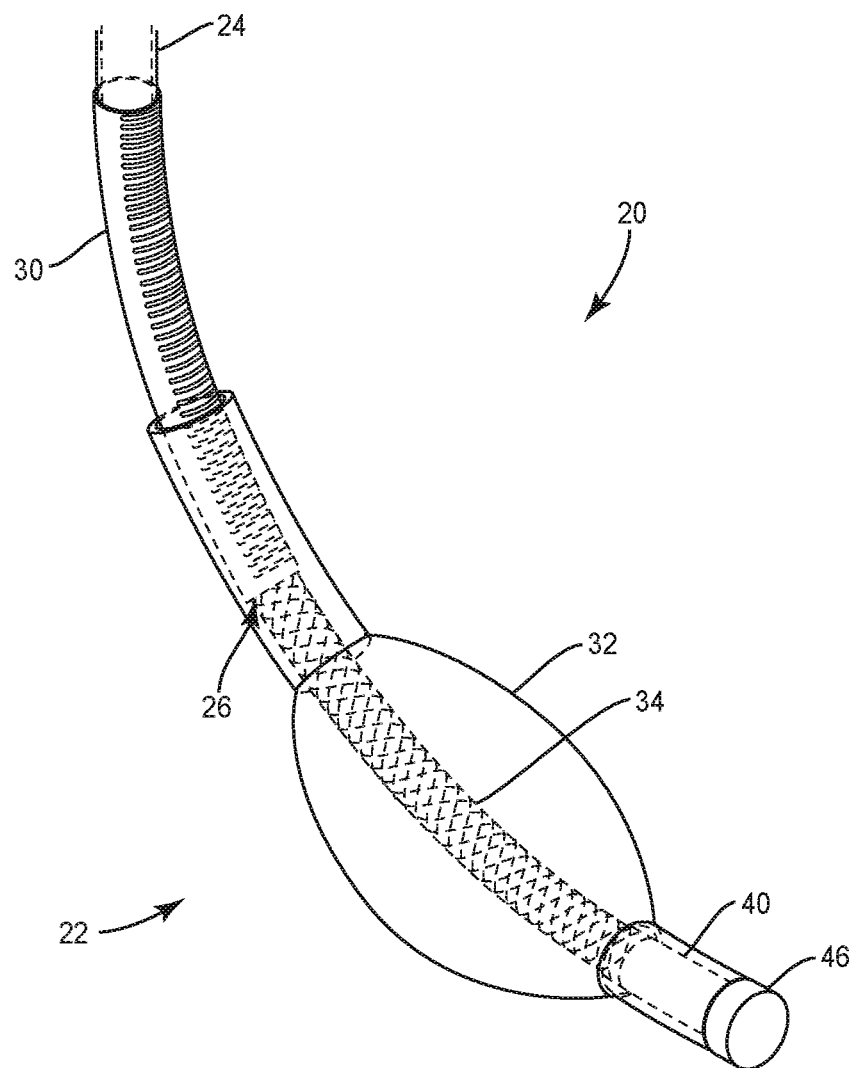
FIG. 3 is a perspective view of one embodiment of the surgical instrument shown in FIG. 1.

In some embodiments, shaft 34 has a non-porous, solid wall configuration (e.g., FIGS. 1 and 1A) and includes one or a plurality of inflation ports 56 that each extend through a thickness of shaft 34 and are in communication with lumen 42. As the inflation material moves through lumen 42, the inflation material will exit lumen 42 through inflation ports 56 and enter chamber 54 to move balloon 32 from an uninflated configuration (e.g., FIG. 1) to an inflated configuration (e.g., FIG. 3). In some embodiments, inflation ports 56 are spaced apart from each other along a length of shaft 34 and/or are spaced apart radially about a circumference of shaft 34, as shown in FIG. 1A.

In embodiments wherein shaft 34 is laser cut, braided, or coiled, the inflation material can enter chamber 54 through gaps or pores in shaft 34 that are not covered or encapsulated by polymer 40. For example, the gaps or pores may be defined by spaces between coils, as can be seen from FIG. 2. Likewise, the gaps or pores may be defined by spaces between interlaced strands that make up the braid, as can be seen from FIG. 3. As the inflation material moves through lumen 42, the inflation material will exit lumen 42 through the gaps or pores in shaft 34 and enter chamber 54 to move balloon 32 from the uninflated configuration to the inflated configuration.

Leg 48 has a thickness t1 defined by the distance between opposite inner and outer surfaces of leg 48 and leg 50 has a thickness t2 defined by the distance between opposite inner and outer surfaces of leg 50, as shown in FIG. 4. In some embodiments, thickness t1 is equal to thickness t2. In some embodiments, thickness t1 is less than thickness t2. In some embodiments, thickness t1 is greater than thickness t2. In some embodiments, leg 48 has a length that is equal to a length of leg 50. In some embodiments, the length of leg 48 is greater than the length of leg 50. In some embodiments, the length of leg 48 is less than the length of leg 50.

Body 52 of balloon 32 includes an inner curve, such as, for example, a concave inner portion 58 that extends from leg 48 to leg 50 and an opposite outer curve, such as, for example, a convex outer portion 60 that extends from leg 48 to leg 50. As shown in FIGS. 4 and 5, portion 58 has a length l1 from leg 48 to leg 50 and portion 60 has a length l2 from leg 48 to leg 50, length l2 being greater than length l1. Portion 58 has a thickness t3 defined by the distance between opposite inner and outer surfaces of portion 58 and portion 60 has a thickness t4 defined by the distance between opposite inner and outer surfaces of portion 60, as also shown in FIG. 5.

When balloon 32 is in the uninflated configuration, thickness t3 is less than thickness t4, as shown in FIG. 4. When balloon 32 is in the inflated configuration, thickness t3 is equal to or substantially equal to thickness t4, as shown in FIG. 5. That is, because length l2 is greater than length l1, as balloon 32 moves from the uninflated configuration to the inflated configuration, portion 60 thins out more than portion 58 thins out so that the thicknesses of portions 58, 60 will be equal or substantially equal when balloon 32 is in the inflated configuration. The configuration of balloon 32 described above also allows balloon 32 to expand uniformly about shaft 34. In some embodiments, thickness t4 is at least 10% greater than thickness t3 when balloon 32 is in the uninflated configuration. In some embodiments, thickness t4 is at least 25% greater than thickness t3 when balloon 32 is in the uninflated configuration. In some embodiments, thickness t4 is 10%, 11%, 12%, 13%, 14%, 15%, 16%, 17%, 18%, 19%, 20%, 21%, 22%, 23%, 24%, 25%, 26%, 27%, 28%, 29%, or 30% greater than thickness t3 when balloon 32 is in the uninflated configuration. In some embodiments, thickness t3 is between about 0.004 inches and about 0.008 when balloon 32 is in the uninflated configuration and thickness t4 is between about 0.006 inches and about 0.01 inches when balloon 32 is in the uninflated configuration. In some embodiments, thickness t3 is 0.006 inches when balloon 32 is in the uninflated configuration and thickness t4 is 0.008 inches when balloon 32 is in the uninflated configuration.

As shown in FIGS. 4 and 5, balloon 32 maintains a curved configuration as balloon 32 moves from the uninflated configuration to the inflated configuration. In some embodiments, balloon 32 inflates uniformly about shaft 32 such that the radius of curvature of axis A remains constant as balloon 32 moves from the uninflated configuration to the inflated configuration. The ability of thickness t3 to be less than thickness t4 when balloon 32 is in the uninflated configuration and thickness t3 to be equal or substantially equal to thickness t4 when balloon 32 is in the inflated configuration will improve the performance of balloon 32 and increase the maximum inflation volume of balloon at higher pressure. As shown in FIGS. 4 and 5, lengths l1, l2 each remain constant as balloon 32 moves from the uninflated configuration to the inflated configuration.

In use, to treat a bone disorder, such as, for example, a spinal fracture, a medical practitioner obtains access to a target location including at least one vertebra, such as, for example, a fractured vertebra V, in any appropriate manner, such as through incision and retraction of tissue. It is envisioned that the balloon catheter system 20 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Figure 6:
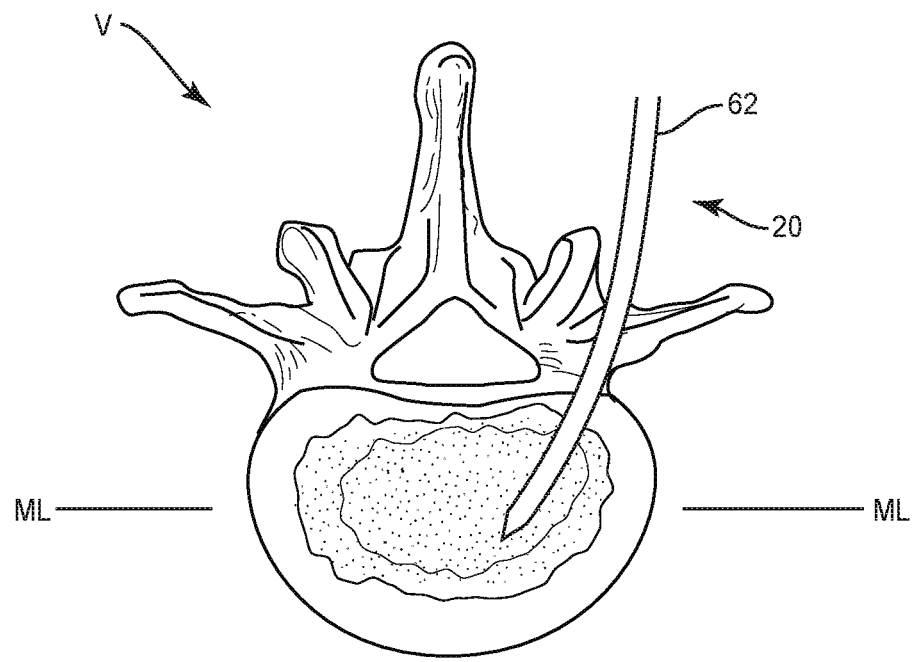
FIG. 6 is a plan view of a surgical instrument in accordance with the principles of the present disclosure being inserted into a vertebra.
Figure 7:
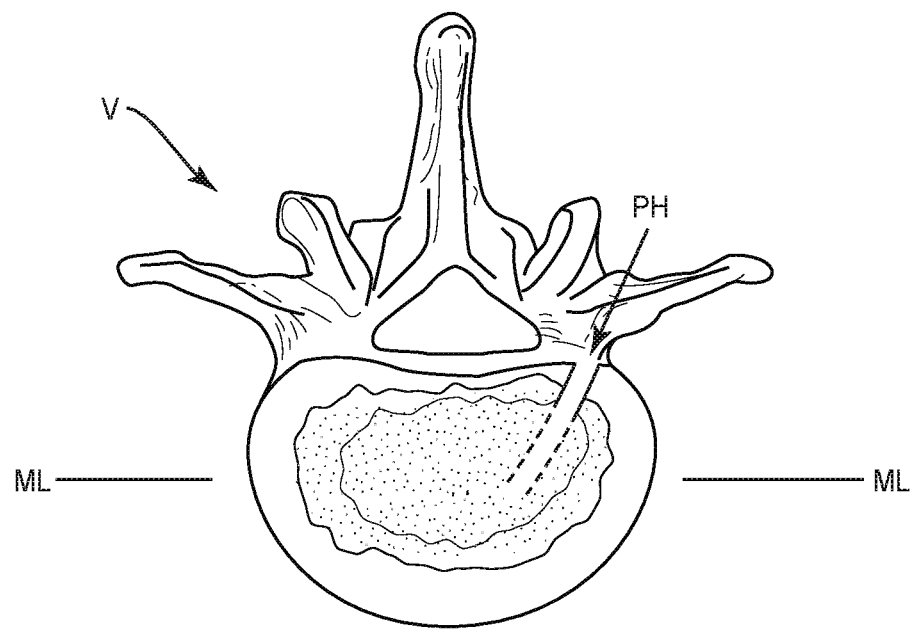
FIG. 7 is a plan view of the vertebra shown in FIG. 6.
Figure 8:
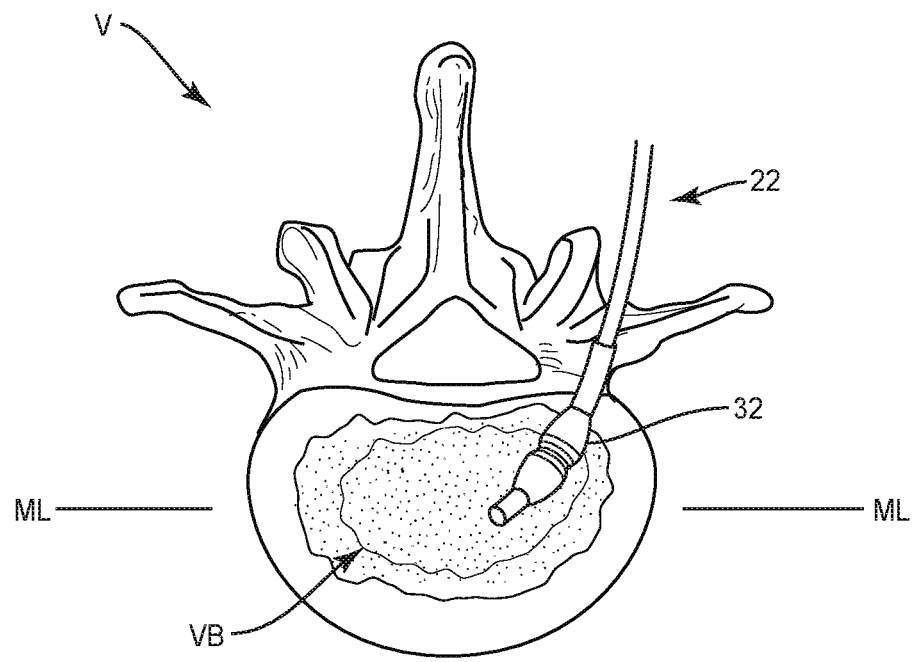
FIG. 8 is a plan view of the surgical instrument shown in FIG. 1 inserted into the vertebra shown in FIG. 6.
Figure 9:
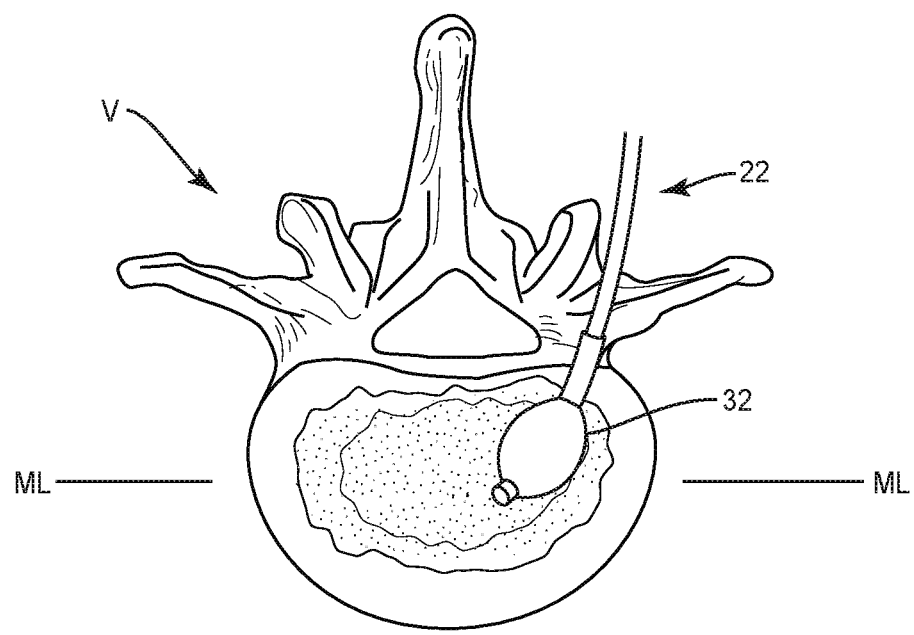
FIG. 9 is a plan view of the surgical instrument shown in FIG. 1 inserted into the vertebra shown in FIG. 6.
Figure 10:
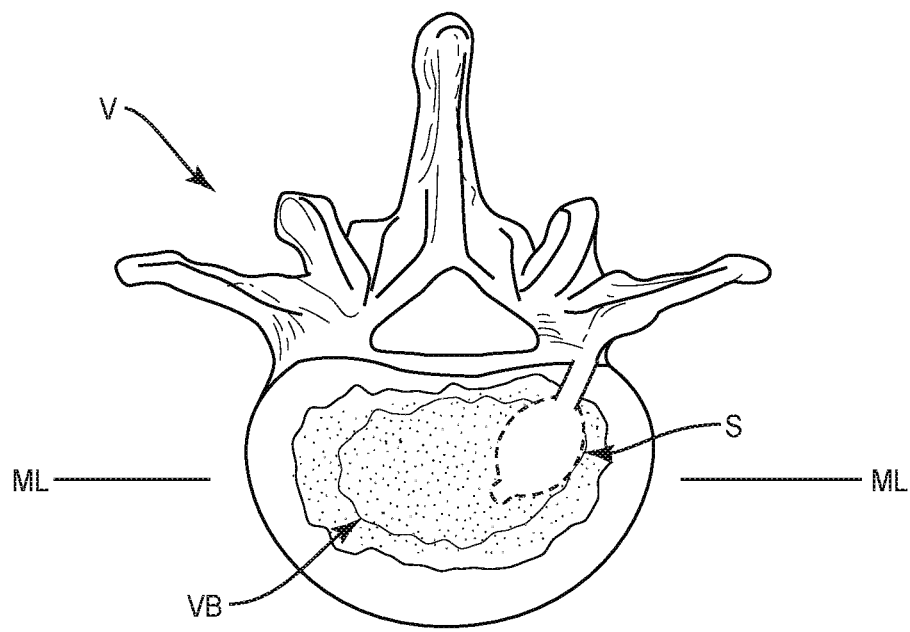
FIG. 10 is a plan view of the vertebra shown in FIG. 6.
Figure 11:
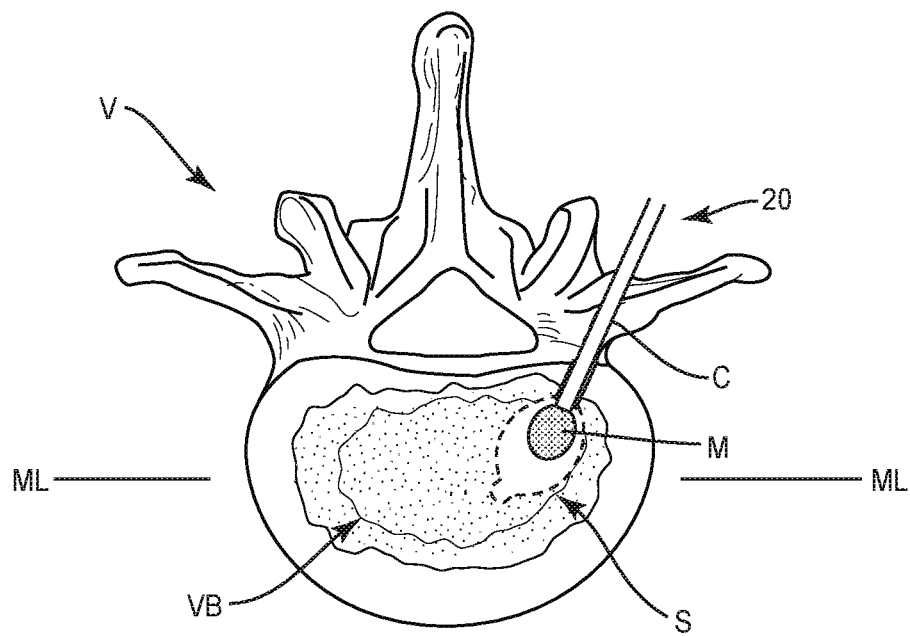
FIG. 11 is a plan view of a surgical instrument in accordance with the principles of the present disclosure being inserted into the vertebra shown in FIG. 6.

As shown in FIG. 6, balloon catheter system 20 includes a curved stylet 62 that is inserted through vertebra V and into a vertebral body VB of vertebra V to access vertebral body VB through a unipedicular approach and create a curved pilot hole PH, as shown in FIG. 7. Curved inflatable bone tamp 22 is inserted through pilot hole PH with balloon 32 in the uninflated configuration such balloon 32 is positioned within vertebral body VB, as shown in FIG. 8. Balloon 32 is moved from the uninflated configuration to the inflated configuration as discussed herein and shown in FIG. 9. As balloon 32 moves from the uninflated configuration to the inflated configuration, balloon 32 creates a void, such as, for example, a space S within vertebral body VB, as shown in FIG. 10. Curved inflatable bone tamp 22 is removed from vertebra V and a cannula C of system 20 is inserted through pilot hole PH and into space S, as shown in FIG. 11. In some embodiments, balloon 32 is moved from the inflated configuration to the uninflated configuration prior to removing curved inflatable bone tamp 22 from vertebra V. In some embodiments, negative pressure, such as, for example, a vacuum is applied to lumen 42 to draw the inflation material out of lumen and move balloon 32 from the inflated configuration to the uninflated configuration. A material, such as, for example, a bone filler material M is inserted through cannula C and into space S, as also shown in FIG. 11. Material M may be inserted into space S until material M fills all or a portion of space S. Cannula C is removed from vertebra V and material M is allowed to cure to treat the fracture by reducing pain from the fracture, stabilizing vertebra V and/or restoring vertebra V back to its normal height.

Figure 12:
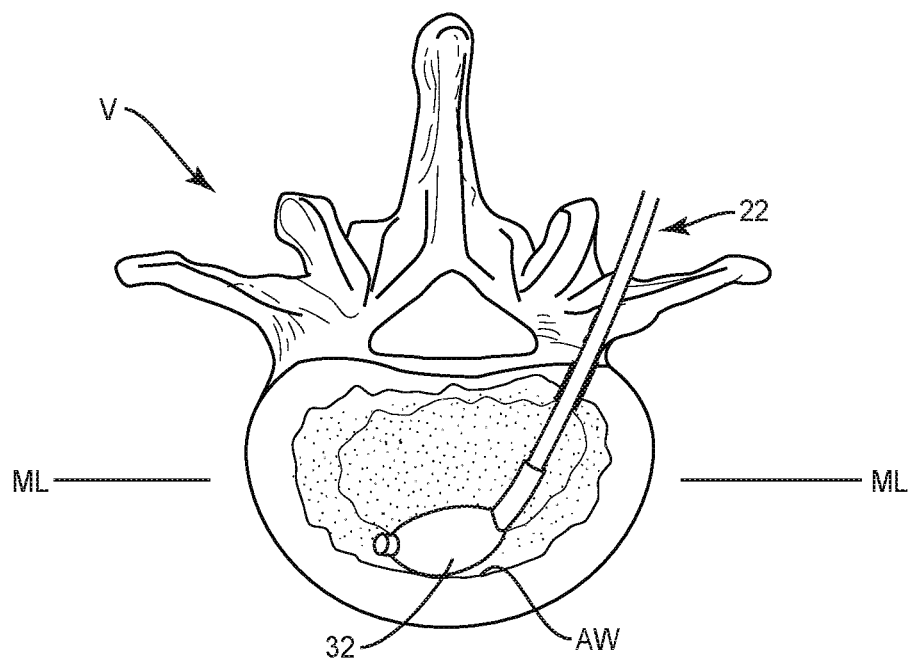
FIG. 12 is a plan view of the surgical instrument shown in FIG. 1 inserted into the vertebra shown in FIG. 6.
Figure 13:
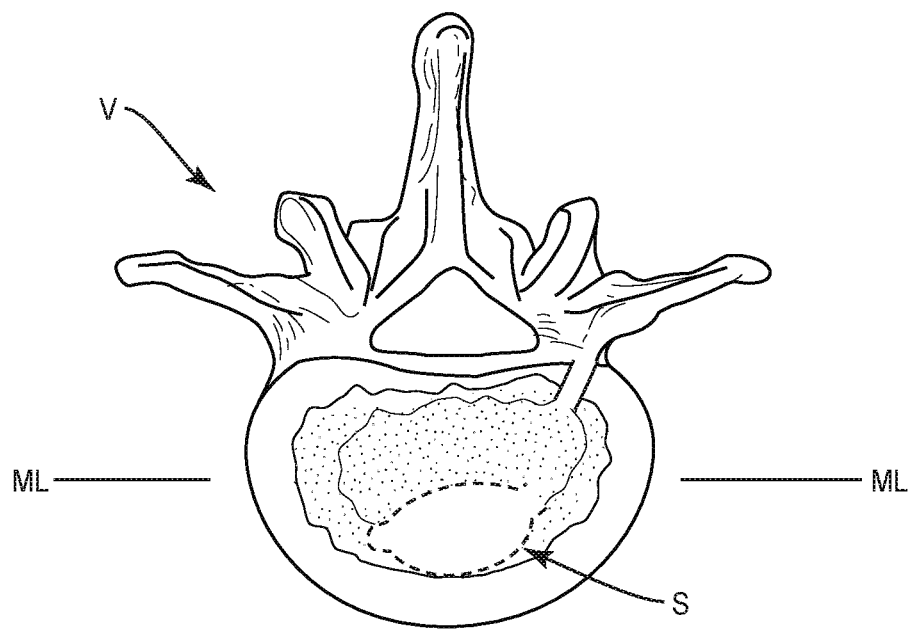
FIG. 13 is a plan view of the vertebra shown in FIG. 6.
Figure 14:
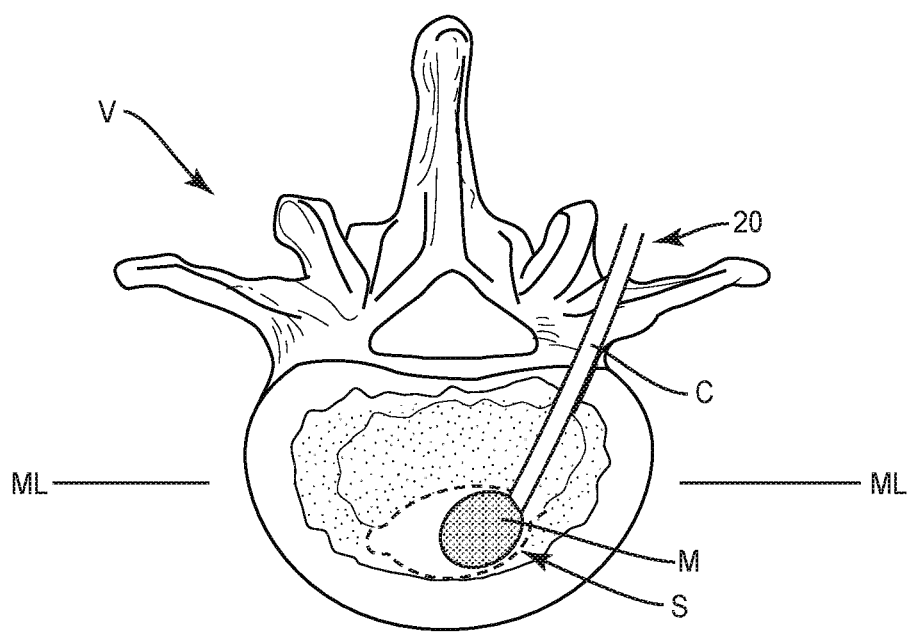
FIG. 14 is a plan view of a surgical instrument in accordance with the principles of the present disclosure being inserted into the vertebra shown in FIG. 6.

In some embodiments, pilot hole PH is oriented to position balloon 32 such that balloon 32 follows an anterior wall AW of vertebral body VB when balloon 32 is inflated within vertebral body VB, as shown in FIG. 12. As shown in FIG. 12, balloon 32 is positioned more anterior than posterior and extends passed midline M of vertebral body VB. In some embodiments, the size and shape of balloon 32 can be customized such that balloon 32 covers at least the anterior ⅔ of vertebral body VB to property treat a vertebral compression fracture of vertebra V. Balloon 32 is moved from the uninflated configuration to the inflated configuration to create space S within vertebral body VB, as shown in FIG. 13. Curved inflatable bone tamp 22 is removed from vertebra V and cannula C is inserted through pilot hole PH and into space S, as shown in FIG. 14. Material M is inserted through cannula C and into space S, as also shown in FIG. 14. Material M may be inserted into space S until material M fills all or a portion of space S.

In some embodiments, a kit containing one or more components of balloon catheter system 20 is provided. The kit may comprise components from any of the embodiments discussed herein. In some embodiments, the kit comprises one or more of the inflation materials discussed herein. In some embodiments, the kit comprises a plurality of cannulas, such as, for example, cannula C having different lengths configured for use with different size patients.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising:
    inserting a stylet through a vertebral body such that the stylet creates a curved pilot hole in the vertebral body;
    inserting a curved inflatable bone tamp through the pilot hole and into an interior of the vertebral body such that a balloon of the inflatable bone tamp extends through a midline of the vertebral body, the balloon having a variable wall thickness between legs of the balloon when the balloon is uninflated;
    inflating the balloon within the vertebral body to create a void within the vertebral body, the balloon having a uniform wall thickness between the legs when the balloon is inflated; and
    filling the void with a bone filling material,
    wherein the inflatable bone tamp comprises an outer shaft defining a passageway and an inner shaft positioned within the passageway, the inner shaft extending between opposite first and second ends, the inner shaft defining a lumen, the inner shaft being curved between the first end and the second end, the balloon having a first leg coupled to the outer shaft and a second leg coupled to the inner shaft such that a material can flow through the lumen and into the balloon to inflate the balloon.

2. A method as recited in claim 1, wherein the balloon inflates uniformly around an axial shaft of the inflatable bone tamp.

3. A method as recited in claim 1, wherein the vertebral body comprises an anterior wall and a posterior wall, the void being created closer to the anterior wall than the posterior wall.

4. A method as recited in claim 1, wherein the vertebral body comprises an anterior wall and a posterior wall, the bone filling material filling at least 50% of an area between the anterior wall and the posterior wall.

5. A method as recited in claim 1, wherein the vertebral body comprises an anterior wall and a posterior wall, the balloon contacting the anterior wall when the balloon is inflated.

6. A method as recited in claim 1, wherein the inflatable bone tamp accesses the interior of the vertebral body via a unipedicular approach.

7. A method as recited in claim 1, wherein the balloon includes a wall comprising an inner portion between the legs having a first thickness when the balloon is uninflated and an outer portion between the legs having a second thickness when the balloon is uninflated, the first thickness being at least 25% greater than the second thickness.

8. A method as recited in claim 1, wherein the inner shaft comprises an inflation port extending through a thickness of the inner shaft, the inflation port being in communication with the lumen such that the material can flow through the lumen and the inflation port and into the balloon.

9. A method as recited in claim 8, wherein the inflation port comprises a plurality of spaced apart inflation ports.

10. A method as recited in claim 8, wherein the inflation port comprises a plurality of spaced apart inflation ports that are spaced apart from each other along a length of the inner shaft.

11. A method as recited in claim 8, wherein the inflation port comprises a plurality of spaced apart inflation ports that are spaced apart radially about a circumference of the inner shaft.

12. A method as recited in claim 1, wherein the balloon has a lobed configuration when the balloon is uninflated and a long conical shape when the balloon is inflated.

13. A method for treating a spine, the method comprising:
    moving a balloon of an inflatable bone tamp into an interior of a vertebral body, the inflatable bone tamp comprising an outer shaft defining a passageway and an inner shaft positioned within the passageway, the inner shaft extending between opposite first and second ends, the inner shaft being curved between the first end and the second end, the inner shaft defining a lumen and an inflation portion in communication with the lumen, the balloon having a first end coupled to the outer shaft and a second end coupled to the inner shaft such that a material can flow through the lumen and the inflation port and into the balloon to inflate the balloon; and inflating the balloon within the interior of the vertebral body to create a void within the vertebral body.

14. A method as recited in claim 13, further comprising filling the void with a bone filling material.

15. A method as recited in claim 14, wherein the vertebral body comprises an anterior wall and a posterior wall, the bone filling material fills at least 50% of an area between the anterior wall and the posterior wall.

16. A method as recited in claim 13, further comprising creating a pilot hole in the vertebral body using a curved stylet, wherein moving the inflatable bone tamp into the interior of the vertebral body comprises moving inflatable bone tamp through the pilot hole and into the interior of the vertebral body.

17. A method as recited in claim 13, wherein the inflation port extends through a thickness of the inner shaft.

18. A method for treating a spine, the method comprising:

moving a balloon of an inflatable bone tamp through a pilot hole in a vertebral body and into an interior of the vertebral body, the inflatable bone tamp comprising an outer shaft defining a passageway and an inner shaft positioned within the passageway, the inner shaft extending between opposite first and second ends, the inner shaft being pre-bent to be curved between the first end and the second end, the inner shaft defining a lumen and an inflation portion in communication with the lumen, the inflation port extending through a thickness of the inner shaft, the balloon having a first end coupled to the outer shaft and a second end coupled to the inner shaft such that a material can flow through the lumen and the inflation port and into the balloon to inflate the balloon;

inflating the balloon within the interior of the vertebral body to create a void within the vertebral body;

removing the balloon from the interior of the vertebral body;

positioning an end of a cannula adjacent to the pilot hole; and inserting a bone filler material through the cannula and into the void to fill at least a portion of the void.

19. A method as recited in claim 18, further comprising deflating the balloon prior to removing the balloon, wherein deflating the balloon comprises applying negative pressure to draw the material out of the balloon and the lumen.

20. A method as recited in claim 18, further comprising creating the pilot hole in the vertebral body using a curved stylet.

* * * * *